US009840598B2

(12) United States Patent
Bauduin et al.

(10) Patent No.: US 9,840,598 B2
(45) Date of Patent: Dec. 12, 2017

(54) METHOD FOR PRODUCING WATER-ABSORBENT POLYMER PARTICLES WITH IMPROVED PROPERTIES

(71) Applicant: BASF SE, Ludwigshafen (DE)

(72) Inventors: Christophe Bauduin, Plankstadt (DE); Thomas Daniel, Waldsee (DE); Asif Karim, Mannheim (DE)

(73) Assignee: BASF SE, Ludwigshafen (DE)

( * ) Notice: Subject to any disclaimer, the term of this patent is extended or adjusted under 35 U.S.C. 154(b) by 19 days.

(21) Appl. No.: 14/407,490

(22) PCT Filed: Jun. 21, 2013

(86) PCT No.: PCT/EP2013/063030
§ 371 (c)(1),
(2) Date: Dec. 12, 2014

(87) PCT Pub. No.: WO2014/005860
PCT Pub. Date: Jan. 9, 2014

(65) Prior Publication Data
US 2015/0119531 A1 Apr. 30, 2015

Related U.S. Application Data

(60) Provisional application No. 61/667,476, filed on Jul. 3, 2012.

(30) Foreign Application Priority Data

Jul. 3, 2012 (EP) .................................. 12174828

(51) Int. Cl.
*C08F 6/00* (2006.01)
*C08J 3/24* (2006.01)
*A61L 15/60* (2006.01)
*A61L 15/22* (2006.01)
*A61L 15/24* (2006.01)
*A61L 15/42* (2006.01)

(52) U.S. Cl.
CPC .............. *C08J 3/245* (2013.01); *A61L 15/22* (2013.01); *A61L 15/24* (2013.01); *A61L 15/42* (2013.01); *A61L 15/60* (2013.01); *C08F 6/008* (2013.01); *C08J 2333/02* (2013.01)

(58) Field of Classification Search
None
See application file for complete search history.

(56) References Cited

U.S. PATENT DOCUMENTS

| 4,666,983 | A | 5/1987 | Tsubakimoto et al. |
|---|---|---|---|
| 4,734,478 | A | 3/1988 | Tsubakimoto et al. |
| 5,004,761 | A | 4/1991 | Yada et al. |
| 5,331,059 | A | 7/1994 | Engelhardt et al. |
| 5,409,771 | A | 4/1995 | Dahmen et al. |
| 5,837,789 | A | 11/1998 | Stockhausen et al. |
| 6,143,821 | A | 11/2000 | Houben |
| 6,239,230 | B1 | 5/2001 | Eckert et al. |
| 6,241,928 | B1 | 6/2001 | Hatsuda et al. |
| 6,472,478 | B1 | 10/2002 | Funk et al. |
| 6,503,979 | B1 | 1/2003 | Funk et al. |
| 6,559,239 | B1 | 5/2003 | Riegel et al. |
| 6,657,015 | B1 | 12/2003 | Riegel et al. |
| 6,849,665 | B2 | 2/2005 | Frenz et al. |
| 7,157,141 | B2 | 1/2007 | Inger et al. |
| 7,183,360 | B2 | 2/2007 | Daniel et al. |
| 7,652,111 | B2 | 1/2010 | Hermeling et al. |
| 7,687,596 | B2 | 3/2010 | Hermeling et al. |
| 7,754,822 | B2 | 7/2010 | Daniel et al. |
| 7,772,420 | B2 | 8/2010 | Hermeling et al. |
| 2002/0128618 | A1 | 9/2002 | Frenz et al. |
| 2005/0118423 | A1* | 6/2005 | Adachi ............. A61L 15/60 428/402 |
| 2011/0042612 | A1 | 2/2011 | Riegel et al. |
| 2011/0059329 | A1* | 3/2011 | Dobrawa ........... A61L 15/60 428/522 |
| 2011/0224361 | A1 | 9/2011 | Daniel et al. |
| 2012/0085971 | A1 | 4/2012 | Daniel et al. |
| 2014/0031473 | A1† | 1/2014 | Nogi |

FOREIGN PATENT DOCUMENTS

| DE | 3314019 A1 | 1/1984 |
|---|---|---|
| DE | 35 23 617 A1 | 1/1986 |
| DE | 38 25 366 A1 | 2/1989 |
| DE | 40 20 780 C1 | 8/1991 |
| DE | 19543368 A1 | 5/1997 |
| DE | 19646484 A1 | 5/1997 |
| DE | 198 07 992 C1 | 7/1999 |
| DE | 198 07 502 A1 | 9/1999 |

(Continued)

OTHER PUBLICATIONS

Third-Party Observation dated Oct. 31, 2014, filed in International Application No. PCT/EP2013/063030.
International Search Report and Written Opinion, International Application No. PCT/EP2013/063030, dated Nov. 18, 2013.
Buchholz et al. (eds.), Modern Superabsorbent Polymer Technology, pp. 71-103, Wiley-VCH (1998).

*Primary Examiner* — Robert C Boyle
(74) *Attorney, Agent, or Firm* — Marshall, Gerstein & Borun LLP

(57) ABSTRACT

The present invention relates to a process for producing water-absorbing polymer particles having an improved profile of properties, comprising thermal surface postcrosslinking in the presence of a salt of a polyvalent metal cation and a complexing anion and subsequent aftertreatment, the aftertreatment comprising coating with a salt of a polyvalent metal cation and a non-complexing anion, and remoisturization with further drying.

8 Claims, No Drawings

(56) References Cited

FOREIGN PATENT DOCUMENTS

| | | |
|---|---|---|
| DE | 198 54 573 A1 | 5/2000 |
| DE | 198 54 574 A1 | 5/2000 |
| DE | 102 04 937 A1 | 8/2003 |
| DE | 10204938 A1 | 8/2003 |
| DE | 10331450 A1 | 1/2005 |
| DE | 10331456 A1 | 2/2005 |
| DE | 10334584 A1 | 2/2005 |
| DE | 10355401 A1 | 6/2005 |
| EP | 0 083 022 A2 | 7/1983 |
| EP | 0450922 A2 | 10/1991 |
| EP | 0 530 438 A1 | 3/1993 |
| EP | 0 543 303 A1 | 5/1993 |
| EP | 0547847 A1 | 6/1993 |
| EP | 559476 A1 | 9/1993 |
| EP | 0632068 A1 | 1/1995 |
| EP | 0937736 A2 | 8/1999 |
| EP | 1199327 A2 | 4/2002 |
| WO | WO-90/15830 A1 | 12/1990 |
| WO | WO-93/21237 A1 | 10/1993 |
| WO | WO-01/38402 A1 | 5/2001 |
| WO | WO-02/32962 A2 | 4/2002 |
| WO | WO-02/055469 A1 | 7/2002 |
| WO | WO-03/031482 A1 | 4/2003 |
| WO | WO-03/078378 A1 | 9/2003 |
| WO | WO-03104299 A1 | 12/2003 |
| WO | WO-03104300 A1 | 12/2003 |
| WO | WO-03104301 A1 | 12/2003 |
| WO | WO-2004035514 A1 | 4/2004 |
| WO | WO-2008/040715 A2 | 4/2008 |
| WO | WO-2008/052971 A1 | 5/2008 |
| WO | WO-2008092842 A1 | 8/2008 |
| WO | WO-2010149735 A1 | 12/2010 |
| WO | WO-2012045705 A1 | 4/2012 |
| WO | WO-2012/107432 A1 | 8/2012 |
| WO | WO-2012102407 A1 | 8/2012 |

\* cited by examiner
† cited by third party

METHOD FOR PRODUCING WATER-ABSORBENT POLYMER PARTICLES WITH IMPROVED PROPERTIES

CROSS-REFERENCE TO RELATED APPLICATIONS

This application is the U.S. national phase of PCT/EP2013/063030, filed Jun. 21, 2013, which claims the benefit of European patent application No. 12174828.9, filed Jul. 3, 2012 and U.S. Provisional Patent Application No. 61/667,476, filed Jul. 3, 2012, incorporated by reference herein in its entirety.

The present invention relates to a process for producing water-absorbing polymer particles having an improved profile of properties, comprising thermal surface postcrosslinking in the presence of a salt of a polyvalent metal cation and a complexing anion and subsequent aftertreatment, the aftertreatment comprising coating with a salt of a polyvalent metal cation and a non-complexing anion, and remoisturization with further drying.

Water-absorbing polymer particles are used to produce diapers, tampons, sanitary napkins and other hygiene articles, but also as water-retaining agents in market gardening. The water-absorbing polymer particles are often also referred to as "absorbent resins", "superabsorbents", "superabsorbent polymers", "absorbent polymers", "absorbent gelling materials", "hydrophilic polymers" or "hydrogels".

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With an increasing amount of crosslinker, the centrifuge retention capacity (CRC) falls and the absorption under a pressure of 21.0 g/cm² (AUL0.3 psi) passes through a maximum.

To improve the use properties, for example saline flow conductivity (SFC), gel bed permeability (GBP) and absorption under a pressure of 49.2 g/cm² (AUL0.7 psi), water-absorbing polymer particles are generally surface postcrosslinked. This increases the level of crosslinking of the particle surface, which can at least partly decouple the absorption under a pressure of 49.2 g/cm² (AUL0.7 psi) and the centrifuge retention capacity (CRC). This surface postcrosslinking can be performed in aqueous gel phase. Preferably, however, dried, ground and screened polymer particles (base polymer) are surface coated with a surface postcrosslinker, thermally surface postcrosslinked and dried. Crosslinkers suitable for that purpose are compounds which can form covalent bonds to at least two carboxylate groups of the water-absorbing polymer particles.

WO 2012/045705 A1 discloses a process for producing thermally surface postcrosslinked water-absorbing polymer particles, wherein the water-absorbing polymer particles are coated before, during or after the thermal surface postcrosslinking with at least one polyvalent metal salt, and the polyvalent metal salt comprises the anion of glycolic acid or the anion of a glycolic acid derivative.

The PCT application with reference number PCT/EP2012/052022 discloses a process for producing water-absorbing polymer particles with high free swell rate, comprising the steps of polymerization, drying, grinding, classification and thermal surface postcrosslinking, remoisturization and drying again.

It was an object of the present invention to provide a process for producing water-absorbing polymer particles having an improved profile of properties.

The object was achieved by a process for producing water-absorbing polymer particles by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, by drying, grinding and classifying the resulting polymer gel, and thermally surface postcrosslinking the classified polymer particles with f) at least one covalent surface postcrosslinker and
g) at least one salt of a polyvalent metal cation and a complexing acid anion, which comprises subsequently aftertreating the surface postcrosslinked polymer particles, the aftertreatment comprising the steps of i) coating with at least one salt of a polyvalent metal cation and a non-complexing acid anion,
ii) increasing the moisture content by 1 to 150% by weight and
iii) drying after the increase in the moisture content.

Process steps i) and ii) can be conducted in any sequence. Preferably, however, step i) is conducted before step ii).

Suitable complexing acid anions for the at least one salt g) are carboxylic anions which, as well as the carboxylic acid group, have at least one functional group suitable for complexation. Such functional groups have free electron pairs without themselves contributing to the charge balance of the polyvalent metal cation, for example hydroxyl and amino groups. Preferred acid anions for the at least one salt g) are glycolate, glycinate, lactate, alanate, citrate, tartrate, tartronate and glycerate.

Suitable polyvalent metal cations for the salt g) are, for example, divalent cations such as $Zn^{2+}$, $Mg^{2+}$, $Ca^{2+}$, $Fe^{2+}$ and $Sr^{2+}$, trivalent cations such as $Al^{3+}$, $Fe^{3+}$, $Cr^{3+}$, and $Mn^{3+}$, tetravalent cations such as $Ti^{4+}$ and $Zr^{4+}$. Preferred polyvalent metal cations are $Al^{3+}$, $Ti^{4+}$ and $Zr^{4+}$. A very particularly preferred salt g) is aluminum lactate.

The amount of polyvalent metal cation used in the salt g) is preferably 0.001 to 1.5% by weight, more preferably 0.005 to 1% by weight and most preferably 0.02 to 0.8% by weight, based in each case on the polymer particles.

Suitable non-complexing acid anions for the salt in step i) are organic acid anions which, aside from the acid group, do not have any functional group suitable for complexation, or inorganic acid anions. Particularly preferred acid anions for the at least one salt in step i) are formate, acetate, propionate, methylsulfonate, sulfate and chloride.

Suitable polyvalent metal cations for the salt in step i) are, for example, divalent cations such as $Zn^{2+}$, $Mg^{2+}$, $Ca^{2+}$, $Fe^{2+}$ and $Sr^{2+}$, trivalent cations such as $Al^{3+}$, $Fe^{3+}$, $Cr^{3+}$, and $Mn^{3+}$, tetravalent cations such as $Ti^{4+}$ and $Zr^{4+}$. Preferred polyvalent metal cations are $Al^{3+}$, $Ti^{4+}$ and $Zr^{4+}$. Very particularly preferred salts in step i) are aluminum sulfate, sodium alum and potassium alum.

The amount of polyvalent metal cation used in the salt in step i) is preferably 0.001 to 1.5% by weight, more preferably 0.005 to 1% by weight and most preferably 0.02 to 0.8% by weight, based in each case on the polymer particles.

The moisture content in step ii) is increased by preferably 2.5 to 100% by weight, more preferably 5 to 50% by weight and very particularly 10 to 25% by weight (remoisturization). The method by which the moisture content is increased is not subject to any restriction. For example, the water-absorbing polymer particles can be contacted with water in liquid or gaseous form, for example by spray application or by ventilating with moist gases (air, nitrogen, etc.). Alternatively, crushed ice or already moist water-absorbing polymer particles can be mixed in. Combinations of different addition forms are also possible, for example an aqueous solution of the salt of polyvalent metal cation and non-complexing acid anion, and steam.

The product temperature during the increase in the water content is, for example, 0 to 140° C., preferably 20 to 120° C., more preferably 50 to 100° C. and most preferably 60 to 90° C.

The delay time between increase in the water content and subsequent drying is uncritical and is, for example, less than 10 days, preferably less than 5 days, more preferably less than one day, especially preferably less than 6 hours and most preferably less than 2 hours.

Subsequently, the water-absorbing polymer particles are dried at temperatures of preferably less than 150° C., more preferably less than 130° C., most preferably less than 110°, down to a moisture content of preferably less than 10% by weight, more preferably less than 7% by weight, most preferably less than 5% by weight.

The subsequent drying can be conducted statically or dynamically, i.e. the water-absorbing polymer particles are or are not moved, for example stirred. Preference is given to dynamic drying. The pressure in the course of drying is likewise uncritical and corresponds, for example, to ambient pressure or less (reduced pressure). However, it is also possible, for drying, to ventilate the water-absorbing polymer particles with a dry gas (air, nitrogen, etc.).

In a preferred embodiment of the present invention, in the course of the inventive drying, the desired moisture content for the end product is established.

The present invention is based on the finding that the vortex and the permeability, i.e. the saline flow conductivity (SFC) and gel bed permeability (GBP), of water-absorbing polymer particles can be improved simultaneously by conducting the thermal surface postcrosslinking in the presence of a salt of a polyvalent metal cation and a complexing acid anion, and subsequently coating the surface postcrosslinked polymer particles with a salt of a polyvalent metal cation and a non-complexing acid anion, and swelling and drying them again. The coating of the surface postcrosslinked polymer particles with the salt of a polyvalent metal cation and a non-complexing acid anion can also be conducted after swelling and drying, i.e. the sequence of the two aftertreatment steps is not essential.

The production of the water-absorbing polymer particles is described in detail hereinafter:

The water-absorbing polymer particles are produced by polymerizing a monomer solution or suspension, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid. Also of good suitability are monomers a) which are produced from renewable raw materials.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 20-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.3 to 0.6% by weight, based in each case on monomer a).

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The monomer solution or suspension is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. It is possible here to combine the process steps of polymerization and drying, as described in WO 2008/040715 A2 and WO 2008/052971 A1.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The resulting polymer gel is dried. The driers are not subject to any restriction. However, the drying of the polymer gel is preferably performed with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

The dried polymer gel is ground and classified, and the apparatus used for grinding may typically be single or multistage roll mills, preferably two or three-stage roll mills, pin mills, hammer mills or vibratory mills.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the saline flow conductivity (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles of excessively large particle size lower the free swell rate. The proportion of excessively large polymer particles should therefore likewise be small.

Excessively large polymer particles are therefore typically removed and recycled into the grinding of the dried polymer gel.

To improve the properties, the polymer particles are thermally surface postcrosslinked. Suitable surface postcrosslinkers f) are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers f) are cyclic carbonates in DE 40 20 780 C1,2-oxazolidone and derivatives thereof, such as 2-hydroxyethyl-2-oxazolidone, in DE 198 07 502 A1, bis- and poly-2-oxazolidinones in DE 198 07 992 C1,2-oxotetrahydro-1,3-oxazine and derivatives thereof in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers f) are ethylene carbonate, propylene carbonate, glyceryl carbonate, ethylene glycol diglycidyl ether, reaction products of polyamides with epichlorohydrin and mixtures of propylene glycol and 1,4-butanediol.

Very particularly preferred surface postcrosslinkers f) are 2-hydroxyethyloxazolidin-2-one, oxazolidin-2-one and 1,3-propanediol.

In addition, it is also possible to use surface postcrosslinkers f) which comprise additional polymerizable ethylenically unsaturated groups, as described in DE 37 13 601 A1.

The amount of surface postcrosslinker f) is preferably 0.001 to 2% by weight, more preferably 0.02 to 1% by weight and most preferably 0.05 to 0.2% by weight, based in each case on the polymer particles.

The thermal surface postcrosslinking is performed in the presence of at least one salt g) of a polyvalent metal cation and a complexing acid anion. The salt g) of a polyvalent metal cation and a complexing acid anion can be applied to the particle surface before or during the thermal surface postcrosslinking.

The surface postcrosslinking is typically performed in such a way that a solution of the surface postcrosslinker f) is sprayed onto the dried polymer particles. After the spray application, the polymer particles coated with surface postcrosslinker f) are dried thermally, and the surface postcrosslinking reaction can take place either before or during the drying.

The spray application of a solution of the surface postcrosslinker f) is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft.

Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers f) are typically used in the form of an aqueous solution. The penetration depth of the surface postcrosslinker f) into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal surface postcrosslinking is preferably performed in contact driers, more preferably shovel driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface postcrosslinking temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

After the thermal surface postcrosslinking, the aftertreatment according to the invention is performed.

Subsequently, the surface postcrosslinked and aftertreated polymer particles can be classified again, excessively small and/or excessively large polymer particles being removed and recycled into the process.

To further improve the properties, the polymer particles can additionally be coated and remoisturized again.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present invention further provides the water-absorbing polymer particles obtainable by the process according to the invention.

The present invention further provides water-absorbing polymer particles obtainable by polymerizing a monomer solution or suspension to give a polymer gel, drying, grinding and classifying the polymer gel to give polymer particles and thermally surface postcrosslinking the polymer particles, the water-absorbing polymer particles having a moisture content of less than 10% by weight, a centrifuge retention capacity of at least 15 g/g, a saline flow conductivity of at least $80 \times 10^{-7}$ cm$^3$ s/g, a gel bed permeability of at least 30 darcies and a vortex of less than 70 s.

The inventive water-absorbing polymer particles typically have a high saline flow conductivity (SFC), a high gel bed permeability (GBP) and a low vortex, for example a saline flow conductivity (SFC) of preferably at least $100 \times 10^{-7}$ cm$^3$ s/g, more preferably of at least $130 \times 10^{-7}$ cm$^3$ s/g and most preferably of 150 to $250 \times 100^{-7}$ cm$^3$ s/g, a gel bed permeability (GBP) of preferably at least 40 darcies, more preferably of at least 45 darcies and most preferably of 50 to 100 darcies, and a vortex of preferably less than 65 s, more preferably of less than 62 s and most preferably of 40 to 60 s.

The inventive water-absorbing polymer particles have a centrifuge retention capacity (CRC) of typically at least 15 g/g, preferably at least 18 g/g, more preferably at least 20 g/g, especially preferably at least 22 g/g and most preferably 23 to 40 g/g. The centrifuge retention capacity (CRC) is determined by EDANA recommended test method No. WSP 241.2-05 "Fluid Retention Capacity in Saline, After Centrifugation".

The inventive water-absorbing polymer particles have an absorption under a pressure of 49.2 g/cm$^2$ of typically at least 15 g/g, preferably at least 18 g/g, more preferably at least 20 g/g, especially preferably at least 22 g/g and most preferably 23 to 40 g/g. The absorption under a pressure of 49.2 g/cm$^2$ is determined analogously to EDANA recommended test method No. WSP 242.2-05 "Absorption Under Pressure, Gravimetric Determination", except that a pressure of 49.2 g/cm$^2$ is established instead of a pressure of 21.0 g/cm$^2$.

The inventive water-absorbing polymer particles have a moisture content of preferably less than 10% by weight, more preferably less than 8% by weight and most preferably of 0.5 to 6% by weight, the moisture content being determined by EDANA recommended test method No. WSP 230.2-05 "Mass Loss Upon Heating".

The present invention further provides hygiene articles comprising inventive water-absorbing polymer particles.

The hygiene articles typically comprise a water-impervious backside, a water-pervious topside and an intermediate absorbent core composed of the inventive water-absorbing polymer particles and fibers, preferably cellulose. The proportion of the inventive water-absorbing polymer particles in the absorbent core is preferably 20 to 100% by weight and more preferably 50 to 100% by weight.

The water-absorbing polymer particles are tested by means of the test methods described below.

The standard test methods designated "WSP" are described in: "Standard Test Methods for the Nonwovens Industry", 2005 edition, published jointly by the Worldwide Strategic Partners EDANA (Avenue Eugène Plasky 157, 1030 Brussels, Belgium, www.edana.org) and INDA (1100 Crescent Green, Cary, N.C. 27518, U.S.A., www.inda.org). This publication is available both from EDANA and from INDA.

Methods:

The measurements should, unless stated otherwise, be carried out at an ambient temperature of 23±2° C. and a relative air humidity of 50±10%. The water-absorbing polymer particles are mixed thoroughly before the measurement.

Moisture Content

The moisture content of the water-absorbing polymer particles is determined by EDANA recommended test method No. WSP 230.2-05 "Mass Loss Upon Heating".

Centrifuge Retention Capacity

The centrifuge retention capacity (CRC) is determined by EDANA recommended test method No. WSP 241.2-05 "Fluid Retention Capacity in Saline, After Centrifugation".

Absorption Under a Pressure of 0.0 g/cm$^2$ (Absorption Under Load)

The absorption under a pressure of 0.0 g/cm$^2$ (AUL0.0 psi) is determined analogously to EDANA recommended test method No. WSP 242.2-05 "Absorption Under Pressure, Gravimetric Determination", except that a pressure of 0.0 g/cm$^2$ (AUL0.0 psi) is established instead of a pressure of 21.0 g/cm$^2$ (AUL0.3 psi).

Absorption Under a Pressure of 21.0 g/cm$^2$ (Absorption Under Load)

The absorption under a pressure of 21.0 g/cm$^2$ (AUL0.3 psi) is determined by EDANA recommended test method No. WSP 242.2-05 "Absorption Under Pressure, Gravimetric Determination".

Absorption Under a Pressure of 49.2 g/cm$^2$ (Absorption Under Load)

The absorption under a pressure of 49.2 g/cm$^2$ (AUL0.7 psi) is determined analogously to EDANA recommended test method No. WSP 242.2-05 "Absorption Under Pressure, Gravimetric Determination", except that a pressure of 49.2 g/cm$^2$ (AUL0.7 psi) is established instead of a pressure of 21.0 g/cm$^2$ (AUL0.3 psi).

Extractables

The content of extractables of the water-absorbing polymer particles is determined by EDANA recommended test method No. WSP 270.2-05 "Extractable".

Free Swell Rate

To determine the free swell rate (FSR), 1.00 g (=W1) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=W2). The time interval required for the absorption, which has been measured with the stopwatch, is designated as t. The disappearance of the last liquid droplet on the surface is determined as the time t.

The free swell rate (FSR) is calculated therefrom as follows:

$$FSR\ [g/g\ s] = W2/(W1 \times t)$$

If the moisture content of the water-absorbing polymer particles, however, is more than 3% by weight, the weight W1 should be corrected to take account of this moisture content.

Vortex 50.0 ml±1.0 ml of a 0.9% by weight aqueous sodium chloride solution are introduced into a 100 ml beaker which comprises a magnetic stirrer bar of size 30 mm×6 mm. A magnetic stirrer is used to stir the sodium chloride solution at 600 rpm. Then 2.000 g±0.010 g of water-absorbing polymer particles are added as rapidly as possible, and the time taken for the stirrer vortex to disappear as a result of the absorption of the sodium chloride solution by the water-absorbing polymer particles is measured. When measuring this time, the entire contents of the beaker may still be rotating as a homogeneous gel mass, but the surface of the gelated sodium chloride solution must no longer exhibit any individual turbulences. The time taken is reported as the vortex.

Saline Flow Conductivity

The saline flow conductivity (SFC) of a swollen gel layer under a pressure of 0.3 psi (2070 Pa) is, as described in EP 0 640 330 A1, determined as the gel layer permeability of a swollen gel layer of water-absorbing polymer particles, the apparatus described on page 19 and in FIG. 8 in the cited patent application having been modified such that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$SFC\ [cm^3 s/g] = (Fg(t=0) \times L0)/(d \times A \times WP)$$

where Fg(t=0) is the flow of NaCl solution in g/s, which is obtained using linear regression analysis of the Fg(t) data of the flow determinations by extrapolation to t=0, L0 is the thickness of the gel layer in cm, d is the density of the NaCl solution in g/cm$^3$, A is the area of the gel layer in cm$^2$, and WP is the hydrostatic pressure over the gel layer in dyn/cm$^2$.

Gel Bed Permeability

The gel bed permeability (GBP) of a swollen gel layer under a pressure of 0.3 psi (2070 Pa) is, as described in US 2005/0256757 (paragraphs [0061] and [0075]), determined as the gel bed permeability of a swollen gel layer of water-absorbing polymer particles.

EXAMPLES

Production of the Base Polymer

Example 1

A base polymer was prepared analogously to the continuous kneader process described in WO 01/38402 A1, in a List Contikneter reactor having a capacity of 6.3 m$^3$ (LIST AG, Arisdorf, Switzerland). For this purpose, acrylic acid was neutralized continuously with sodium hydroxide solution and diluted with water, such that the degree of neutralization of the acrylic acid was 69 mol % and the solids content (=sodium acrylate and acrylic acid) of this solution was approx. 40.0% by weight. The crosslinker used was acrylated glyceryl triacrylate with triple ethoxylation overall (Gly-3 EO-TA), which had been prepared according to US 2005/0176910, in an amount of 0.348% by weight based on acrylic acid monomer. The crosslinker was added continuously to the monomer stream. For the calculation of the acrylic acid monomer content, the sodium acrylate present was considered theoretically as acrylic acid. The initiation was effected by likewise continuous addition of aqueous solutions of the initiators sodium persulfate (0.195% by weight based on acrylic acid monomer), hydrogen peroxide (0.002% by weight based on acrylic acid monomer) and ascorbic acid (0.0031% by weight based on acrylic acid monomer).

The polymer gel obtained was dried on a belt drier, then the drier cake was crushed, ground by means of a roll mill and finally screened off to a particle size of 150 to 850 μm.

The base polymer thus prepared had the following properties:

CRC=36.0 g/g

Extractables (16 h)=14.0% by weight

Particle Size Distribution

| >850 μm | <0.1% by weight |
|---|---|
| 600-850 μm | 3.61% by weight |
| 300-600 μm | 77.55% by weight |
| 150-300 μm | 18.8% by weight |
| <150 μm | <0.1% by weight |

Example 2

A further base polymer was prepared analogously to the continuous kneader process described in WO 01/38402 A1, in a List Contikneter reactor having a capacity of 6.3 m³ (LIST AG, Arisdorf, Switzerland). For this purpose, acrylic acid was neutralized continuously with sodium hydroxide solution and diluted with water, such that the degree of neutralization of the acrylic acid was 72 mol % and the solids content (=sodium acrylate and acrylic acid) of this solution was approx. 38.8% by weight. The crosslinker used was Gly-3EO-TA in an amount of 0.484% by weight based on acrylic acid monomer. The crosslinker was added continuously to the monomer stream. The initiation was effected by likewise continuous addition of aqueous solutions of the initiators sodium persulfate (0.14% by weight based on acrylic acid monomer), hydrogen peroxide (0.001% by weight based on acrylic acid monomer) and ascorbic acid (0.002% by weight based on acrylic acid monomer).

The polymer gel obtained was dried on a belt drier, then the drier cake was crushed, ground on a roll mill and finally screened off to a particle size of 150 to 850 μm.

The base polymer thus prepared had the following properties:

CRC=33.6 g/g

Extractables (16 h)=12.2% by weight

Particle Size Distribution

| >850 μm | 0.02% by weight |
|---|---|
| 600-850 μm | 26.1% by weight |
| 300-600 μm | 48.3% by weight |
| 150-300 μm | 24.9% by weight |
| <150 μm | <0.1% by weight |

Surface Postcrosslinking of the Base Polymer

Example 3

In a Schugi® Flexomix 100 D (Hosokawa-Micron B.V., Doetinchem, the Netherlands) with gravimetric metering and continuous mass flow-controlled liquid metering via a liquid nozzle, base polymer from example 1 was sprayed with a surface postcrosslinking solution. The surface postcrosslinker solution was a mixture of 0.07% by weight of N-(2-hydroxyethyl)oxazolidinone, 0.07% by weight of 1,3-propanediol, 0.50% by weight of aluminum trilactate, 0.70% by weight of propylene glycol, 1.00% by weight of isopropanol and 2.22% by weight of water, based in each case on the base polymer.

The moist base polymer was transferred directly from the Schugi® Flexomix, falling into a NARA Paddle-Dryer® NPD 1.6 W (GMF Gouda, Waddinxveen, the Netherlands). The throughput rate of base polymer was 60 kg/h (dry), and the product temperature of the steam-heated drier at the drier outlet was approx. 188° C. The drier was connected upstream of a cooler which rapidly cooled the product to approx. 50° C. The residence time in the drier was defined via the constant throughput rate of the base polymer and the weir height of 70%, and was approx. 60 minutes. The residence time necessary is determined by preliminary tests, which help to determine the constant metering rate which leads to the desired profile of properties. This is necessary in the continuous process since the bulk density changes constantly during the reaction drying. The properties of the resulting polymer are in table 1.

Example 4

In a Schugi® Flexomix 100 D (Hosokawa-Micron B.V., Doetinchem, the Netherlands) with gravimetric metering and continuous mass flow-controlled liquid metering via a liquid nozzle, base polymer from example 2 was sprayed with a surface postcrosslinking solution. The surface postcrosslinker solution was a mixture of 0.11% by weight of Denacol® EX810 (ethylene glycol diglycidyl ether), 0.26% by weight of aluminum sulfate, 1.00% by weight of propylene glycol and 2.00% by weight of water, based in each case on the base polymer.

The moist base polymer was transferred directly from the Schugi® Flexomix, falling into a NARA Paddle-Dryer® NPD 1.6 W (GMF Gouda, Waddinxveen, the Netherlands). The throughput rate of base polymer was 60 kg/h (dry), and the product temperature of the steam-heated drier at the drier outlet was approx. 180° C. The drier was connected upstream of a cooler which rapidly cooled the product to approx. 50° C. The residence time in the drier was defined via the constant throughput rate of the base polymer and the weir height of 70%, and was approx. 60 minutes. The residence time necessary is determined by preliminary tests, which help to determine the constant metering rate which leads to the desired profile of properties. This is necessary in the continuous process since the bulk density changes constantly during the reaction drying. The properties of the resulting polymer are in table 1.

TABLE 1

Surface postcrosslinking of the base polymer

| Ex. | CRC [g/g] | AUL0.7 psi [g/g] | AUL0.3 psi [g/g] | AUL0.0 psi [g/g] | SFC [$10^{-7}$ cm$^3$g/s] | GBP [darcies] | Vortex [s] | FSR [g/gs] |
|---|---|---|---|---|---|---|---|---|
| 3*) | 24.2 | 22.0 | 26.0 | 35.4 | 119 | 17 | 86 | 0.17 |
| 4*) | 29.7 | 21.8 | 28.3 | 42.8 | 45 | 22 | 95 | 0.20 |

*)comparative example

Aftertreatment after Surface Postcrosslinking

Example 5

A Pflugschar® M5RMK shovel drier of capacity 5 l (Gebr. Lödige Maschinenbau GmbH; Paderborn, Germany) was initially charged with 1.2 kg of dry polymer from example 3. Subsequently, while stirring (60 rpm), within approx. 120 seconds, a nitrogen-driven two-phase nozzle was used to spray on a solution of 2% by weight of water and 0.50% by weight of aluminum sulfate, based in each case on the polymer used, with mixing for a total of 15 minutes. Finally, the product was screened through a 850 µm screen in order to remove lumps. The properties of the resulting polymer are in table 2.

Example 6

A Pflugschar® M5RMK shovel drier of capacity 5 l (Gebr. Lödige Maschinenbau GmbH; Paderborn, Germany) was initially charged with 1.2 kg of dry polymer from example 4. Subsequently, while stirring (60 rpm), within approx. 120 seconds, a nitrogen-driven two-phase nozzle was used to spray on a solution of 2% by weight of water and 0.50% by weight of aluminum sulfate, based in each case on the polymer used, with mixing for a total of 15 minutes. Finally, the product was screened through a 850 µm screen in order to remove lumps. The properties of the resulting polymer are in table 2.

Example 7

A Pflugschar® M5RMK shovel drier of capacity 5 l (Gebr. Lödige Maschinenbau GmbH; Paderborn, Germany) was initially charged with 1.2 kg of dry polymer from example 3. Subsequently, while stirring (60 rpm), within approx. 120 seconds, a nitrogen-driven two-phase nozzle was used to spray on a solution of 2% by weight of water and 0.50% by weight of aluminum trilactate, based in each case on the polymer used, with mixing for a total of 15 minutes. Finally, the product was screened through a 850 µm screen in order to remove lumps. The properties of the resulting polymer are in table 2.

Example 8

100 g in each case of the surface postcrosslinked polymer particles from example 3 were mixed at 90° C. and a relative air humidity of 75% in a climate-controlled cabinet for 90 minutes. The water absorption during the storage was approx. 6 to 8% by weight. Subsequently, the sample was introduced into a 500 ml plastic bottle and the mixture was homogenized by means of a Turbula mixer for 10 minutes. The sample was introduced into a round-bottom flask with baffles and dried at 80° C. under reduced pressure (27 to 30 mbar) in a rotary evaporator for 15 minutes. This was followed by screening off to a particle size of less than 850 µm. The dried polymer particles were analyzed. The results are summarized in table 2.

Example 9

The procedure was as in example 8. Instead of polymer from example 3, polymer from example 5 was used. The results are summarized in table 2.

Example 10

The procedure was as in example 8. Instead of polymer from example 3, polymer from example 6 was used. The results are summarized in table 2.

Example 11

The procedure was as in example 8. Instead of polymer from example 3, polymer from example 7 was used. The results are summarized in table 2.

Example 12

A Pflugschar® M5RMK shovel drier of capacity 5 l (Gebr. Lödige Maschinenbau GmbH; Paderborn, Germany) was initially charged with 1.2 kg of dry polymer from example 8. Subsequently, while stirring (60 rpm), within approx. 120 seconds, a nitrogen-driven two-phase nozzle was used to spray on a solution of 2% by weight of water and 0.50% by weight of aluminum sulfate, based in each case on the polymer used, with mixing for a total of 15 minutes. Finally, the product was screened through a 850 µm screen in order to remove lumps. The properties of the resulting polymer are in table 2.

TABLE 2

Aftertreatment after surface postcrosslinking

| Ex. | CRC [g/g] | AUL0.7 psi [g/g] | AUL0.3 psi [g/g] | AUL0.0 psi [g/g] | SFC [$10^{-7}$ cm$^3$g/s] | GBP [darcies] | Vortex [s] | FSR [g/gs] | Moisture content [% by wt.] |
|---|---|---|---|---|---|---|---|---|---|
| 5*) | 24.1 | 21.2 | 26.0 | 39.7 | 145 | 54 | 84 | 0.18 | 3.0 |
| 6*) | 28.4 | 20.4 | 26.8 | 45.1 | 54 | 88 | 80 | 0.22 | 4.0 |
| 7*) | 25.7 | 22.5 | 26.5 | 37.0 | 166 | 19 | 106 | 0.16 | 3.1 |
| 8*) | 25.3 | 22.9 | 26.6 | 36.1 | 130 | 16 | 90 | 0.19 | 5.2 |

TABLE 2-continued

Aftertreatment after surface postcrosslinking

| Ex. | CRC [g/g] | AUL0.7 psi [g/g] | AUL0.3 psi [g/g] | AUL0.0 psi [g/g] | SFC [$10^{-7}$ cm$^3$g/s] | GBP [darcies] | Vortex [s] | FSR [g/gs] | Moisture content [% by wt.] |
|---|---|---|---|---|---|---|---|---|---|
| 9 | 24.9 | 21.5 | 26.4 | 39.6 | 187 | 53 | 58 | 0.22 | 1.6 |
| 10*) | 28.3 | 19.6 | 26.0 | 43.0 | 46 | 97 | 57 | 0.28 | 7.3 |
| 11*) | 25.3 | 21.0 | 25.6 | 35.9 | 182 | 21 | 74 | 0.19 | 6.3 |
| 12 | 25.3 | 21.6 | 26.1 | 39.6 | 186 | 81 | 60 | 0.19 | 6.2 |

*)comparative example

TABLE 3

Overview of process conditions

| Examples | Step A | Step B | Step C |
|---|---|---|---|
| 1*) | NO | NO | NO |
| 2*) | NO | NO | NO |
| 3*) | YES: Al lactate | NO | NO |
| 4*) | NO: Al sulfate | NO | NO |
| 5*) | YES: Al lactate | YES: Al sulfate | NO |
| 6*) | NO: Al sulfate | YES: Al sulfate | NO |
| 7*) | YES: Al lactate | NO: Al lactate | NO |
| 8*) | YES: Al lactate | NO | YES |
| 9 | YES: Al lactate | YES: Al sulfate | YES |
| 10*) | NO: Al sulfate | YES: Al sulfate | YES |
| 11*) | YES: Al lactate | NO: Al lactate | YES |
| 12 | YES: Al lactate | YES: Al sulfate | YES |

Step A: surface postcrosslinking in the presence of a complexing acid anion
Step B: aftertreatment with a non-complexing acid anion
Step C: increasing the moisture content with subsequent drying
Al sulfate: aluminum sulfate
Al lactate: aluminum trilactate
*)comparative example The results show that only on fulfillment of all process steps essential to the invention, i.e., surface postcrosslinking in the presence of a complexing acid anion, aftertreatment with a non-complexing acid anion and increasing the moisture content with subsequent drying, are water-absorbing polymer particles with high saline flow conductivity (SFC), high gel bed permeability (GBP) and low vortex obtained.

The invention claimed is:

1. A process for producing water-absorbing polymer particles comprising polymerizing a monomer solution or suspension comprising
   a) at least one ethylenically unsaturated monomer which bears an acid group and may be at least partly neutralized,
   b) at least one crosslinker,
   c) at least one initiator,
   d) optionally one or more ethylenically unsaturated monomer copolymerizable with the monomer mentioned under a) and
   e) optionally one or more water-soluble polymer,
drying, grinding, and classifying a resulting polymer gel, and thermally surface postcrosslinking the classified polymer particles with
   f) at least one covalent surface postcrosslinker, and
   g) at least one salt of a polyvalent metal cation and a complexing acid anion selected from the group consisting of glycolate, glycinate, lactate, alanate, citrate, tartrate, tartronate, and glycerate,
which comprises subsequently aftertreating the surface postcrosslinked polymer particles, the aftertreatment comprising
   i) coating with at least one salt of a polyvalent metal cation and a non-complexing acid anion selected from the group consisting of formate, acetate, propionate, methylsulfonate, sulfate, and chloride,
   ii) increasing the moisture content by 1 to 150% by weight, and
   iii) drying after the increase in the moisture content.

2. The process according to claim 1, wherein step ii) is conducted before step i).

3. The process according to claim 1, wherein the classified polymer particles are coated with 0.02 to 0.8% by weight of the polyvalent metal cation.

4. The process according to claim 1, wherein the surface postcrosslinked polymer particles are coated with 0.02 to 0.8% by weight of the polyvalent metal cation.

5. The process according to claim 1, wherein the polyvalent metal cation is selected from the group of $Al^{3+}$, $Ti^{4+}$, and $Zr^{4+}$.

6. The process according to claim 1, wherein the surface postcrosslinked polymer particles, after increasing the moisture content, are dried at a temperature of less than 150° C.

7. The process according to claim 1, wherein the surface postcrosslinked polymer particles, after increasing the moisture content, are dried down to a moisture content of less than 10% by weight.

8. The process according to claim 1, wherein the water-absorbing polymer particles have a centrifuge retention capacity of at least 15 g/g.

* * * * *